United States Patent
Maury et al.

(10) Patent No.: US 6,696,273 B2
(45) Date of Patent: Feb. 24, 2004

(54) FEBP1 PROTEIN: VECTOR, HOST CELLS AND METHOD FOR MAKING FEBP1 PROTEIN

(75) Inventors: Isabelle Maury, Vitry sur Seine (FR); Luc Mercken, Saint Maur (FR); Alain Fournier, Chatenay Malabry (FR)

(73) Assignee: Aventis Pharma S.A., Antony (FR)

( * ) Notice: Subject to any disclaimer, the term of this patent is extended or adjusted under 35 U.S.C. 154(b) by 69 days.

(21) Appl. No.: 09/780,996

(22) Filed: Feb. 9, 2001

(65) Prior Publication Data

US 2002/0061553 A1 May 23, 2002

Related U.S. Application Data

(60) Provisional application No. 60/198,500, filed on Apr. 18, 2000.

(30) Foreign Application Priority Data

Feb. 10, 2000 (FR) .............................................. 00/01628

(51) Int. Cl.$^7$ ......................... C12N 15/11; C12N 15/85; C12N 15/86; C07K 5/00; C07K 14/00
(52) U.S. Cl. .............. 435/69.1; 435/252.3; 435/254.11; 435/325; 530/300; 530/350; 536/23.1
(58) Field of Search .............................. 536/23.5, 23.1; 435/370.1, 69.1, 325, 252.1, 252.3, 254.11; 530/300, 350

(56) References Cited

U.S. PATENT DOCUMENTS

| | | | | | |
|---|---|---|---|---|---|
| 5,389,526 | A | * | 2/1995 | Slade et al. ................. | 435/69.1 |
| 5,928,882 | A | * | 7/1999 | Sabo et al. .................... | 435/7.1 |
| 6,214,582 | B1 | * | 4/2001 | Marcu ......................... | 435/69.1 |

FOREIGN PATENT DOCUMENTS

WO    WO 99/26961    6/1999

OTHER PUBLICATIONS

Zambrano et al. (Mar. 7, 1997) "Interaction of the Phosphotyrosine Interaction/Phosphotyrosine Binding–related Domains of Fe65 with Wild–type and Mutant Alzheimer's b–Amyloid Precursor Protein." The Journal of Biological Chemistry 272(10): 6399–6405.*
Bradford Chemical Neurobiology: An Introduction to Neurochemistry (1986) Chapter 9 W.H. Freeman and Company, New York.*
Voet & Voet Biochemistry 2$^{nd}$ Ed. (1995) Chapter 13 John Wiley & Sons, Inc. New York.*
Lam & Breakefield (2000) Hybrid Vetror Designs to Control the Delivery, Fate, and Expression of Transgenes. J Gene Med 2:395–408.*
Kochanek et al. (2001) High–Capacity 'Gutless' Adenoviral Vectors. Current Opinion in Molecular Therapeutics. 3(5): 454–463.*
Skolnick & Fetrow (2000) From Genes to Protein Structure and Function: Novel Applications of Computational Approaches in the Genomic Era. Trends in Biotech 18(1):34–39.*
Bork (2000) Powers and Pitfalls in Sequence Analysis: The 70% Hurdle. Genome Research 10:398–400.*
Doerks (1998) Protein Annotation: Detective Work for Function Prediction. TIG 14(6): 248–250.*
Bork (1996) Go Hunting in Sequence Databases but Watch out for Traps. TIG 12(10): 425–427.*
Friedmann (1992) Gene Therapy of Cancer Through Restoration of Tumor–Suppressor Functions? Cancer 70:1810–1817.*
Brenner (1999) Errors in Genome Annotation. TIG 15(4): 132–133.*
Smith & Zhang (1997) The Challenges of Genome Sequence Annotation or "The Devil is in the Details". Nature Biotechnology 15: 1222–1223.*
Anderson (1984) Prospects for Human Gene Therapy. Science 226: 401–409.*
Gutierrez et al. (1992) Gene Therapy for Cancer. The Lancet 339: 715–721.*
Verma and Somia (1997) Gene Therapy–Promises, Problems, and Prospects. Nature 389:239–241.*
Goodman & Gilman's The Pharmacological Basis of Therapeutics 9$^{th}$ Ed. (1996) McGraw–Hill New York Chapter 5: Gene–Based Therapy by Eck & Wilson.*
English Translation of Borg et al., *PTB, An Important Protein–Protein Interaction Domain of the "domino effect" of Signal Transduction* Medecine/Sciences 13:647–656 (1997).
Pinol–Roma et al, A novel heterogenous nuclear RNP protein with a unique distribution on nascent transcripts., J. Cell. Biol. 109:2575–2587 (1989).
Rasmussen et al, Microsequences of 145 proteins recorded in the two–dimensional gel protein database of normal epidermal keratinocytes, Electrophoresis 13:960–969 (1992).
Zambrano et al, The Fe65 adaptor protein interacts through its PID1 domain with the transcription factor CP2/LSF/LBP1, J. Biol. Chem. 273/32 (20128–20133) (1998).
McLoughlin et al, the intracellular cytoplasmic domain of the Alzheimer's disease amyloid precursor protein interacts with phosphotyrosine–binding domain proteins in the yeast two–hybrid system., FEBS Letters (1996) 397/2–3 (197–200).

(List continued on next page.)

*Primary Examiner*—Elizabeth Kemmerer
*Assistant Examiner*—Christopher James Nichols

(57) ABSTRACT

The present invention relates to novel compounds and their pharmaceutical or diagnostic use, or use as a pharmacological target. More particularly, the present invention describes the identification of partners of the FE65 protein and the use of these partners, or of any compound which is capable of modulating, at least partially, their interaction with FE65, for regulating the activity of FE65, and in particular the phenomenon of intracellular transport or of endocytosis of the APP.

11 Claims, No Drawings

OTHER PUBLICATIONS

Fiore et al, The regions of the Fe65 protein homologous to the phosphotyrosine interaction phosphotyrosine binding domain of Shc bind the intracellular domain of Alzheimer's amyloid precursor protein, J. Biol. Chem. 270(53):30853–30856 (1995).

Borg et al, The phosphotyrosine interaction domains of X11 and FE65 bind to distinct sites on the YENPTY motif of amyloid precursor protein, Molec. and Cell. Biol. 16(11):6229–6241 (1996).

* cited by examiner

SEQUENCE LISTING

<160> NUMBER OF SEQ ID NOS: 9

<210> SEQ ID NO 1
<211> LENGTH: 447
<212> TYPE: DNA
<213> ORGANISM: Homo sapiens

<400> SEQUENCE: 1

```
cccccacgga ataccaaccc agggatcaag tgtttcgccg tgcgctccct aggctgggta      60
gagatgaccg aggaggagct ggcccctgga cgcagcagtg tggcagtcaa caattgcatc     120
```

```
cgtcagctct cttaccacaa aaacaacctg catgacccca tgtctggggg ctggggggaa    180
ggaaaggatc tgctactgca gctggaggat gagacactaa agctagtgga gccacagagc    240
caggcactgc tgcacgccca acccatcatc agcatccgcg tgtggggcgt cgggcgggac    300
agtggaaggg actttgccta cgtagctcgt gataagctga cccagatgct caagtgccac    360
gtgtttcgct gtgaggcacc tgccaagaac atcgccacca gcctgcatga gatctgctct    420
aagatcatgg ccgaacggcg taatgcc                                       447
```

```
<210> SEQ ID NO 2
<211> LENGTH: 149
<212> TYPE: PRT
<213> ORGANISM: Homo sapiens

<400> SEQUENCE: 2

Pro Pro Arg Asn Thr Asn Pro Gly Ile Lys Cys Phe Ala Val Arg Ser
1               5                   10                  15

Leu Gly Trp Val Glu Met Thr Glu Glu Leu Ala Pro Gly Arg Ser
            20                  25                  30

Ser Val Ala Val Asn Asn Cys Ile Arg Gln Leu Ser Tyr His Lys Asn
        35                  40                  45

Asn Leu His Asp Pro Met Ser Gly Gly Trp Gly Glu Gly Lys Asp Leu
    50                  55                  60

Leu Leu Gln Leu Glu Asp Glu Thr Leu Lys Leu Val Glu Pro Gln Ser
65                  70                  75                  80

Gln Ala Leu Leu His Ala Gln Pro Ile Ile Ser Ile Arg Val Trp Gly
                85                  90                  95

Val Gly Arg Asp Ser Gly Arg Asp Phe Ala Tyr Val Ala Arg Asp Lys
            100                 105                 110

Leu Thr Gln Met Leu Lys Cys His Val Phe Arg Cys Glu Ala Pro Ala
        115                 120                 125

Lys Asn Ile Ala Thr Ser Leu His Glu Ile Cys Ser Lys Ile Met Ala
    130                 135                 140

Glu Arg Arg Asn Ala
145

<210> SEQ ID NO 3
<211> LENGTH: 28
<212> TYPE: DNA
<213> ORGANISM: Artificial Sequence
<220> FEATURE:
<223> OTHER INFORMATION: PCR primer

<400> SEQUENCE: 3
cttcccgggt cccccacgga ataccaac                                       28

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4
ggggtcgacg gcattacgcc gttcggc                                        27

<210> SEQ ID NO 5
<211> LENGTH: 18
<212> TYPE: DNA
```

```
<213> ORGANISM: Artificial Sequence
<220> FEATURE:
<223> OTHER INFORMATION: GAL4TA oligonucleotide

<400> SEQUENCE: 5
ccactacaat ggatgatg                                                      18

<210> SEQ ID NO 6
<211> LENGTH: 1047
<212> TYPE: DNA
<213> ORGANISM: Homo sapiens

<400> SEQUENCE: 6
gtgttggggg cttgcaacgc agtgaactac gcagccgaca accaaatata cattgctggt         60
cacccagctt ttgtcaacta ctctaccagc cagaagatct cccgccctgg ggactcggat        120
gactcccgga gcgtgaacag tgtgcttctc tttaccatcc tgaacccatt tattcgatc         180 accacggatg ttctttacac tatctgtaat ccttgtggcc ctgtccagag aattgtcatt        240
ttcaggaaga atggagttca ggcgatggtg gaatttgact cagttcaaag tgcccagcgg        300
gccaaggcct ctctcaatgg ggctgatatc tattctggct gttgcactct gaagatcgaa        360
tacgcaaagc ctacacgctt gaatgtgttc aagaatgatc aggatacttg ggactacaca        420
aaccccaatc tcagtggaca aggtgaccct ggcagcaacc caacaaacg ccagaggcag         480 cccctctcc tgggagatca ccccgcagaa tatggagggc cccacggtgg gtaccacagc         540
cattaccatg atgagggcta cgggcccccc ccacctcact acgaagggag aaggatgggt        600
ccaccagtgg ggggtcaccg tcggggccca agtcgctacg cccccagta tgggcacccc        660 ccacccccctc ccccaccacc cgagtatggc cctcacgccg acagccctgt gctcatggtc        720
tatggcttgg atcaatctaa gatgaactgt gaccgagtct tcaatgtctt ctgcttatat        780
ggcaatgtgg agaaggtgaa attcatgaaa agcaagccgg gggccgccat ggtggagatg        840
gctgatggct acgctgtaga ccgggccatt acccacctca acaacaactt catgtttggg        900
cagaagctga atgtctgtgt ctccaagcag ccagccatca tgcctggtca gtcatacggg        960
ttggaagacg ggtcttgcag ttacaaagac ttcagtgaat cccggaacaa tcggttctcc       1020
accccagagc aggcagccaa gaaccgc                                           1047

<210> SEQ ID NO 7
<211> LENGTH: 349
<212> TYPE: PRT
<213> ORGANISM: Homo sapiens

<400> SEQUENCE: 7

Val Leu Gly Ala Cys Asn Ala Val Asn Tyr Ala Ala Asp Asn Gln Ile
1               5                   10                  15

Tyr Ile Ala Gly His Pro Ala Phe Val Asn Tyr Ser Thr Ser Gln Lys
            20                  25                  30

Ile Ser Arg Pro Gly Asp Ser Asp Ser Arg Ser Val Asn Ser Val
        35                  40                  45

Leu Leu Phe Thr Ile Leu Asn Pro Ile Tyr Ser Ile Thr Thr Asp Val
    50                  55                  60

Leu Tyr Thr Ile Cys Asn Pro Cys Gly Pro Val Gln Arg Ile Val Ile
65                  70                  75                  80

Phe Arg Lys Asn Gly Val Gln Ala Met Val Glu Phe Asp Ser Val Gln
                85                  90                  95

Ser Ala Gln Arg Ala Lys Ala Ser Leu Asn Gly Ala Asp Ile Tyr Ser
```

```
                100              105              110
Gly Cys Cys Thr Leu Lys Ile Glu Tyr Ala Lys Pro Thr Arg Leu Asn
            115              120              125

Val Phe Lys Asn Asp Gln Asp Thr Trp Asp Tyr Thr Asn Pro Asn Leu
    130              135              140

Ser Gly Gln Gly Asp Pro Gly Ser Asn Pro Asn Lys Arg Gln Arg Gln
145              150              155              160

Pro Pro Leu Leu Gly Asp His Pro Ala Glu Tyr Gly Pro His Gly
                165              170              175

Gly Tyr His Ser His Tyr His Asp Glu Gly Tyr Gly Pro Pro Pro
            180              185              190

His Tyr Glu Gly Arg Arg Met Gly Pro Pro Val Gly Gly His Arg Arg
        195              200              205

Gly Pro Ser Arg Tyr Gly Pro Gln Tyr Gly His Pro Pro Pro Pro
    210              215              220

Pro Pro Pro Glu Tyr Gly Pro His Ala Asp Ser Pro Val Leu Met Val
225              230              235              240

Tyr Gly Leu Asp Gln Ser Lys Met Asn Cys Asp Arg Val Phe Asn Val
                245              250              255

Phe Cys Leu Tyr Gly Asn Val Glu Lys Val Lys Phe Met Lys Ser Lys
            260              265              270

Pro Gly Ala Ala Met Val Glu Met Ala Asp Gly Tyr Ala Val Asp Arg
        275              280              285

Ala Ile Thr His Leu Asn Asn Asn Phe Met Phe Gly Gln Lys Leu Asn
    290              295              300

Val Cys Val Ser Lys Gln Pro Ala Ile Met Pro Gly Gln Ser Tyr Gly
305              310              315              320

Leu Glu Asp Gly Ser Cys Ser Tyr Lys Asp Phe Ser Glu Ser Arg Asn
                325              330              335

Asn Arg Phe Ser Thr Pro Glu Gln Ala Ala Lys Asn Arg
            340              345

<210> SEQ ID NO 8
<211> LENGTH: 1275
<212> TYPE: DNA
<213> ORGANISM: Homo sapiens
<220> FEATURE:
<221> NAME/KEY: misc_feature
<223> OTHER INFORMATION: n= a or g or c or t/u

<400> SEQUENCE: 8 cgggggatg tggatgatgc tggggactgt tctggggcca ggtataatga ctggtctgat      60
gatgatgatg acagcaatga gagcaagagt atagtatggt acccaccttg ggctcggatt    120
gggactgaag ctggaaccag agctagggcc agggcaaggg ccagggctac ccgggcacgt    180
cgggctgtcc agaaacgggc ttcccccaat tcagatgata ccgttttgtc ccctcaagag    240
ctacaaaagg ttctttgctt ggttgagatg tctgaaaagc cttatattct tgaagcagct    300
ttaattgctc tgggtaacaa tgctgcttat gcatttaaca gagatattat tcgtgatctg    360
ggtggtctcc caattgtcgc aaagattctc aatactcggg atcccatagt taaggaaaag    420
gctttaattg tcctgaataa cttgagtgtg aatgctgaaa atcagcgcag gcttaaagta    480
tacatgaatc aagtgtgtga tgacacaatc acttctcgct tgaactcatc tgtgcagctt    540
gctggactga gattgcttac aaatatgact gttactaatg agtatcagca catgcttgct    600
aattccattt ctgactttt tcgtttattt tcagcgggaa atgaagaaac caaacttcag    660
```

```
gttctgaaac tccttttgaa tttggctgaa atccagcca tgactaggga actgctcagg      720
gcccaagtac catcttcact gggctccctc tttaataaga aggagaacaa agaagttatt      780
cttaaacttc tggtcatatt tgagaacata atgataatt tcaaatggga agaaaatgaa       840
cctactcaga atcaattcgg tgaaggttca cttttttct ttttaaaaga atttcaagtg       900
tgtgctgata aggntctggg aatagaaagt caccatgatt ttttggtgaa agtaaaagtt      960
ggaaaattca tggccaaact tgctgaacat atgttcccaa agagccagga ataacacctt     1020
gattttgtaa tttagaagca acacacattg taaactattc attttctcca ccttgtttat     1080
atggtaaagg aatcctttca gctgccagtt ttgaataatg aatatcatat tgtatcatca     1140
atgctgatat ttaactgagt tggtctttag gtttaagatg gataaatgaa tatcactact     1200
tgttctgaaa acatgtttgt tgcttttat ctcgctgcct agattgaaat attttgctat      1260
ttcttctggc taaag                                                     1275
```

<210> SEQ ID NO 9
<211> LENGTH: 337
<212> TYPE: PRT
<213> ORGANISM: Homo sapiens
<220> FEATURE:
<221> NAME/KEY: misc_feature
<223> OTHER INFORMATION: X=G, D, V, or A

<400> SEQUENCE: 9

```
Arg Gly Asp Val Asp Asp Ala Gly Asp Cys Ser Gly Ala Arg Tyr Asn
1               5                   10                  15

Asp Trp Ser Asp Asp Asp Asp Ser Asn Glu Ser Lys Ser Ile Val
            20                  25                  30

Trp Tyr Pro Pro Trp Ala Arg Ile Gly Thr Glu Ala Gly Thr Arg Ala
        35                  40                  45

Arg Ala Arg Ala Arg Ala Thr Arg Ala Arg Ala Val Gln
    50                  55                  60

Lys Arg Ala Ser Pro Asn Ser Asp Asp Thr Val Leu Ser Pro Gln Glu
65                  70                  75                  80

Leu Gln Lys Val Leu Cys Leu Val Glu Met Ser Glu Lys Pro Tyr Ile
                85                  90                  95

Leu Glu Ala Ala Leu Ile Ala Leu Gly Asn Asn Ala Ala Tyr Ala Phe
            100                 105                 110

Asn Arg Asp Ile Ile Arg Asp Leu Gly Gly Leu Pro Ile Val Ala Lys
        115                 120                 125

Ile Leu Asn Thr Arg Asp Pro Ile Val Lys Glu Lys Ala Leu Ile Val
    130                 135                 140

Leu Asn Asn Leu Ser Val Asn Ala Glu Asn Gln Arg Arg Leu Lys Val
145                 150                 155                 160

Tyr Met Asn Gln Val Cys Asp Asp Thr Ile Thr Ser Arg Leu Asn Ser
                165                 170                 175

Ser Val Gln Leu Ala Gly Leu Arg Leu Leu Thr Asn Met Thr Val Thr
            180                 185                 190

Asn Glu Tyr Gln His Met Leu Ala Asn Ser Ile Ser Asp Phe Phe Arg
        195                 200                 205

Leu Phe Ser Ala Gly Asn Glu Glu Thr Lys Leu Gln Val Leu Lys Leu
    210                 215                 220

Leu Leu Asn Leu Ala Glu Asn Pro Ala Met Thr Arg Glu Leu Leu Arg
225                 230                 235                 240
```

-continued

```
Ala Gln Val Pro Ser Ser Leu Gly Ser Leu Phe Asn Lys Lys Glu Asn
            245                 250                 255

Lys Glu Val Ile Leu Lys Leu Leu Val Ile Phe Glu Asn Ile Asn Asp
            260                 265                 270

Asn Phe Lys Trp Glu Glu Asn Glu Pro Thr Gln Asn Gln Phe Gly Glu
            275                 280                 285

Gly Ser Leu Phe Phe Phe Leu Lys Glu Phe Gln Val Cys Ala Asp Lys
        290                 295                 300

Xaa Leu Gly Ile Glu Ser His His Asp Phe Leu Val Lys Val Lys Val
305                 310                 315                 320

Gly Lys Phe Met Ala Lys Leu Ala Glu His Met Phe Pro Lys Ser Gln
                325                 330                 335

Glu
```

FEBP1 PROTEIN: VECTOR, HOST CELLS AND METHOD FOR MAKING FEBP1 PROTEIN

PRIORITY CLAIM

This Application claims the benefit of French Application No. FR00/01628 filed on Feb. 10, 2000 and U.S. Provisional Application No. 60/198,500 filed on Apr. 18, 2000.

Alzheimer's disease (AD) is a neuro-degenerative disease which affects a large proportion of the elderly population. This disease is characterized, clinically speaking, by the loss of cognitive functions, and, neuropathologically speaking, by the presence in the brain of intracellular neurofibrilliary deposits and of extracellular deposits of the β-amyloid (Aβ) peptide, which form amyloid plaques (Yankner, 1996). Amyloid plaques are mainly composed of the Aβ peptides having 40 or 42 amino acids, which are generated by a proteolytic process from the precursor protein of the β-amyloid peptide (APP) (Golde et al., 1992). The extracellular deposits of Aβ are specific for AD. They are the early and invariable feature of all the forms of AD, including the hereditary forms. These hereditary forms of the disease appear relatively early on (between 40 and 60 years of age) and are due to mutations in the APP gene and in the presenilin 1 (PS1) and presenilin 2 (PS2) genes. The mutations in these three genes induce changes in the proteolysis of the APP, which lead to an overproduction of Aβ and to the early appearance of the pathology and of the symptoms, which are similar to those of the sporadic forms of AD.

Internalization of the membrane APP is a step which is required for the process of proteolysis of the APP (Koo and Squazzo, 1994), which depends on its cytoplasmic domain. Specifically, the deletion of this region of the protein, or the presence of point mutations in the sequence Tyr-Glu-Asn-Pro-Thr-Tyr in the cytoplasmic domain of the APP, induces a considerable decrease in the production of the β-amyloid peptide (Perez et al., 1999). Several proteins have been identified as interacting with the cytoplasmic domain of the APP; these proteins might thus participate in the regulation of the proteolytic process of the APP and thus in the production of the β-amyloid peptide. The two protein families FE65 and X11 which interact with the sequence Tyr-Glu-Asn-Pro-Thr-Tyr of the cytoplasmic domain of the APP (Borg et al., 1996, 1998; Bressler et al., 1996; Duilio et al., 1998; Fiore et al., 1995; Guenette et al., 1996; McLoughlin and Miller, 1996; Mercken et al., 1998; Tanahashi and Tabira, 1999a, 1999b and 1999c) should be mentioned. The FE65 protein family consists of three members which are called FE65, COFE65/FE65L1 and FE65L2. The X11 protein family also consists of three members, which are called X11α, X11β, and X11γ. These two protein (Mercken et al., 1998; Sabo et al., 1999), whereas the overexpression of X11 induces a decrease in the production of the Aβ peptide (Borg et al., 1998; Sastre et al., 1998).

Analysis of the primary structure of FE65 indicates that this protein probably plays the role of adapter. Specifically, FE65 contains three protein domains which are involved in protein—protein interactions: a WW domain in the amino-terminal half and two PTB domains (PhosphoTyrosine Binding domain), called PTB1 and PTB2, in the carboxy-terminal half. The construction of deletions has shown that the PTB2 domain of FE65 is involved in the interaction with the cytoplasmic domain of the APP. The WW domain interacts with at least five proteins, of which two have been identified as being the protein Mena (Mammalian homolog of Enabled) (Ermekova et al., 1997). In addition, the PTB1 domain of FE65 interacts with the transcription factor CP2/LSF/LBP1 (Zambrano et al., 1997) and with the receptor LRP (LDL receptor-Related Protein) (Trommsdorff et al., 1998). The role of these proteins in the physiological function of FE65 is not known to date.

The elucidation of the exact role of the FE65 protein in the process of production of the β-amyloid peptide thus constitutes a major asset for the understanding of, and the therapeutic approach to, Alzheimer's disease and more generally neurodegenerative diseases.

The present invention lies in the identification of partners of the FE65 protein which interact with this protein under physiological conditions. These partners represent novel pharmacological targets for the manufacture or the investigation of compounds which are capable of modulating the activity of FE65, in particular its activity on the production of the β-amyloid peptide. These proteins, the antibodies, the corresponding nucleic acids and the specific probes or primers can also be used for detecting or for assaying the proteins in biological samples, in particular nervous tissue samples. These proteins or nucleic acids can also be used in therapeutic approaches, to modulate the activity of FE65 and any compound according to the invention which is capable of modulating the interaction between FE65 and the polypeptides of the invention.

The present invention results more particularly from the revelation, by the applicant, of two human proteins which interact with the PTB1 domain of FE65 (represented on the sequence SEQ ID No.:1 and 2). Thus, the present invention shows that the central region of the protein hnRNPL interacts with the PTB1 domain of FE65. It also describes the identification of a novel protein, termed FEBP1 (FE65 Binding PTB1 domain protein), which is capable of interacting with the PTB1 domain of FE65.

The present invention also results from the identification and from the characterization of specific regions of the hnRNPL and FEBP1 proteins above, which are involved in the modulation of the function of the FE65 protein. The demonstration of the existence of these proteins and of regions which are involved in their function makes it possible in particular to prepare novel compounds and/or compositions which can be used as pharmaceutical agents, and to develop industrial methods for screening such compounds.

A first subject of the invention thus relates to compounds which are capable of modulating, at least partially, the interaction of the hnRNPL and/or FEBP1 proteins (or homologs thereof) with the PTB1 domain of FE65, or of interfering with this reaction.

The interference of a compound according to the invention can reveal itself in various ways. The compound according to the invention can slow, inhibit or stimulate, at least partially, the interaction between an hnRNPL and/or FEBP1 protein (or homologs thereof) and the PTB1 domain of FE65. They are preferably compounds which are capable of modulating this interaction in vitro, for example in a system of double-hybrid type or in any acellular system for detecting an interaction between two polypeptides. The compounds according to the invention are preferably compounds which are capable of modulating, at least partially, this interaction, preferably by increasing or inhibiting this interaction by at least 20%, more preferably by at least 50%, with respect to a control in the absence of the compound.

For the purposes of the present invention, the name of the proteins hnRNPL and FEBP1 covers the proteins per se and all homologous forms thereof. "Homologous form" is intended to refer to any proteins which are equivalent to the protein under consideration, of various cellular origin and in particular derived from cells of human origin, or other organisms, and which possess an activity of the same type. Such homologs also comprise the natural variants of the proteins indicated, in particular the polymorphic or splicing variants. The homologous proteins (or polypeptides) can be obtained, for example, by experiments of hybridization between the coding nucleic acids. For the purposes of the invention, a sequence of this type only has to have a significant percentage of identity to lead to a physiological behavior which is comparable to those of the hnRNPL and/or FEBP1 proteins as claimed.

According to a particular embodiment, the compounds of the invention are capable of binding at the level of the domain of interaction between the hnRNPL and/or FEBP1 proteins and the PTB1 domain of FE65.

The compounds according to the present invention can be of varied nature and origin. In particular, they can be compounds of peptide, nucleic acid (i.e. comprising a string of bases, in particular a DNA or an RNA molecule), lipid or saccharide type, an antibody, etc. and, more generally, any organic or inorganic molecule.

According to a first variant, the compounds of the invention are of peptide nature. The term "peptide" refers to any molecule comprising a string of amino acids, such as for example a peptide, a polypeptide, a protein, an antibody (or antibody fragment or derivative), which if necessary is modified or combined with other compounds or chemical groups. In this respect, the term "peptide" refers more specifically to a molecule comprising a string of at most 50 amino acids, more preferably at most 40 amino acids. A polypeptide comprises preferably from 50 to 500 amino acids, or more. A protein is a polypeptide corresponding to a natural molecule.

According to a first preferred embodiment, the peptide compounds of the invention comprise a portion of the peptide sequence of the hnRNPL protein and/or of the FEBP1 protein and/or of derivatives thereof. It is more particularly a portion of the sequence of the hnRNPL protein and/or of the FEBP1 protein, said proteins being characterized, respectively, in that they comprise the sequences SEQ ID No. 7 and SEQ ID No. 9.

Peptide compounds according to the invention are more preferably compounds comprising a region whose sequence corresponds to all or a functional portion of the site of interaction of the hnRNPL protein and/or the FEBP1 protein with the PTB1 domain of FE65. Such compounds, in particular peptides, constitute competitors of hnRNPL and/or FEBP1, and are capable of modulating, at least partially, the interaction between the hnRNPL protein and/or the FEBP1 protein (and/or homologous forms) and the PTB1 domain of FE65. They are more preferably peptide compounds comprising residues 1 to 349 of the sequence SEQ ID No.:7 or residues 1 to 337 of the sequence SEQ ID No.:9. As indicated in the examples, these sequences comprise at least one portion of the central region of the hnRNPL (residues 116 to 464) and FEBP1 proteins, and are capable of interacting specifically with the PTB1 domain of FE65 and not with the PTB2 domain of FE65.

In a specific embodiment, the compound is a fragment of the sequence SEQ ID No.:7, of at least 5 amino acids, preferably at least 9 amino acids, comprising the sequence Asn-Pro-Ile-Tyr (residues 55 to 58).

According to another preferred embodiment, the peptide compounds of the invention are compounds which are derived from the hnRNPL protein or from the FEBP1 protein (and/or from the homologous forms) and which bear an effector region which has been made nonfunctional. Such peptide compounds can be obtained by deletion, mutation or disruption of at least this effector region in the hnRNPL protein and/or the FEBP1 protein and/or the homologous forms. Such modifications can be carried out for example by in vitro mutagenesis, by introduction of additional elements or of synthetic sequences, or by deletions or substitutions of the original elements. These polypeptides thus have the capacity to bind the FE65 protein, but cannot induce a functional signal, at least not to the same degree as the native proteins.

According to a specific embodiment, it is a polypeptide which comprises the sequence SEQ ID No.:7 or SEQ ID No.:9 and which bears at least one mutation in the effector region.

According to a specific embodiment, it is a polypeptide which comprises the sequence SEQ ID No.:7 or SEQ ID No.:9 and which bears at least one deletion in the effector region.

According to a specific embodiment, it is a polypeptide which comprises the sequence SEQ ID No.:7 or SEQ ID No.:9 and which bears at least one insertion in the effector region.

Another specific subject of the invention lies in the FEBP1 protein, or any fragment or derivative of this protein. It is more particularly any polypeptide comprising the sequence SEQ ID No.:9 or a derivative or fragment of this sequence, even more preferably any polypeptide comprising at least 10 consecutive residues of the sequence SEQ ID No.:9 or of a derivative of this sequence, even more preferably comprising at least the residues which are involved in the binding to the PTB1 domain of FE65.

Another subject of the invention lies in a polypeptide comprising the sequence SEQ ID No.:7.

The term "derivative" refers more particularly, for the purposes of the present invention, to any sequences which differ from the sequence under consideration because of a degeneracy of the genetic code, which is obtained by one or more modifications of genetic and/or chemical nature, as well as any peptide which is encoded by a sequence which hybridizes with the nucleic acid sequences SEQ ID No.:6 or 8, or fragments thereof, and which has the capacity to interfere with the interaction between the hnRNPL protein and/or the FEBP1 protein and/or a homolog thereof, and the PTB1 domain of FE65. The expression "modification of genetic and/or chemical nature" can be understood to mean any mutation, substitution, deletion, addition and/or modification of one or more residues. The term "derivative" also comprises the sequences which are homologous to the sequence under consideration, which are derived from other cellular sources and in particular from cells of human origin, or from other organisms, and which have an activity of the same type. Such homologous sequences can be obtained by hybridization experiments. The hybridizations can be carried out using nucleic acid libraries, using the native sequence or a fragment thereof as probe, under variable conditions of hybridization (Sambrook et al., cf. General techniques of molecular biology). Moreover, the term "fragment" or "portion" refers to any portion of the molecule under consideration, which comprises at least 5 consecutive residues, preferably at least 9 consecutive residues, even more preferably at least 15 consecutive residues.

Such derivatives or fragments can be generated with different aims, such as in particular that of increasing their therapeutic efficacy or of reducing their side effects, or that of conferring on them novel pharmacokinetic and/or biological properties.

When a derivative or fragment as defined above is prepared, its biological activity on the binding of the hnRNPL protein and/or of the FEBP1 protein, and/or of the homologous forms, to their binding site on the PTB1 domain of FE65 can be demonstrated. Any technique which is known to persons skilled in the art can of course be used for this, as is explained in the experimental section (double-hybrid, immobilization on a column, acellular system, cellular system, etc.).

Generally, the compounds of the invention can be any fragment of the hnRNPL or FEBP1 proteins or of the peptide compounds indicated above. Such fragments can be generated in various ways. In particular, they can be synthesized chemically, on the basis of the sequences given in the present application, using the peptide synthesizers known to persons skilled in the art. They can also be synthesized genetically, by expression in a host cell of a nucleotide sequence encoding the desired peptide. In this case, the nucleotide sequence can be prepared chemically, using an oligonucleotide synthesizer, on the basis of the peptide sequence given in the present application and of the genetic code. The nucleotide sequence can also be prepared from sequences given in the present application, by enzymatic cleavage, ligation, cloning, etc., according to the techniques known to persons skilled in the art, or by screening of DNA libraries with probes which are developed from these sequences.

Other peptides according to the invention are peptides which are capable of competing with the peptides defined above, for the interaction with their cellular target. Such peptides can be synthesized in particular on the basis of the sequence of the peptide under consideration, and their capacity for competing with the peptides defined above can be determined.

According to another particular embodiment, the compounds of the invention are antibodies, or antibody fragments or derivatives. Thus, another subject of the invention lies in polyclonal or monoclonal antibodies or fragments of antibodies, which are directed against a peptide compound or a protein as defined above. Such antibodies can be generated by methods known to persons skilled in the art. In particular, these antibodies can be prepared by immunizing an animal against a peptide of the invention, by sampling blood, and by isolating the antibodies. These antibodies can also be generated by preparing hybridomas according to the techniques known to persons skilled in the art.

More preferably, the antibodies or antibody fragments of the invention have the capacity to modulate, at least partially, the interaction of the peptide compounds defined above or of the hnRNPL and/or FEBP1 proteins with the PTB1 domain of FE65, and can be used to modulate the activity of FE65.

Moreover, these antibodies can also be used to detect and/or to assay the expression of the claimed peptides in biological samples, and consequently to provide information on their activation state.

The antibody fragments or derivatives are, for example, Fab or Fab'2 fragments, single-chain (ScFv) antibodies, etc. They are in particular any fragment or derivative which conserves the antigenic specificity of the antibodies from which they are derived.

The antibodies according to the invention are more preferably capable of binding the hnRNPL and/or FEBP1 proteins which comprise respectively the sequence SEQ ID Nos.:7 or 9, in particular the region of these proteins which is involved in the interaction with FE65. These antibodies (or fragments or derivatives) are more preferably capable of binding an epitope which is present in the sequence between residues 1 and 349 of SEQ ID No.:7 or between residues 1 and 337 of SEQ ID No. 6.

The invention also relates to compounds which are not peptides or which are not exclusively peptides, which are capable of interfering with the abovementioned interaction, and to their use as pharmaceutical agents. It is in fact possible, from the active protein motifs described in the present application, to produce molecules which are modulators of the activity of the hnRNPL and/or FEBP1 proteins, which are not exclusively peptides, and which are compatible with pharmaceutical use, in particular by duplicating the active motifs of the peptides with a structure which is not a peptide, or which is not exclusively peptide in nature.

A subject of the present invention is also any nucleic acid which encodes a peptide compound according to the invention. It can in particular be a sequence comprising all or part of the sequences which are presented in SEQ ID No.:6 and in SEQ ID No.:8, or of derivatives thereof. "Derived sequence" is intended to mean, for the purposes of the present invention, any sequence which hybridizes with the sequences which are presented in SEQ ID No.:6 and in SEQ ID No.:8, or with a fragment of these sequences, which encodes a peptide according to the invention, as well as the sequences which result from these latter by degeneracy of the genetic code. The various nucleotide sequences of the invention may or may not be of artificial origin. They can be genomic, cDNA or RNA sequences, hybrid sequences, or synthetic or semi-synthetic sequences. These sequences can be obtained either by screening DNA libraries (cDNA library, genomic DNA library) or by chemical synthesis or by mixed methods which include the chemical or enzymatic modification of sequences which are obtained by screening of libraries. The abovementioned hybridization is preferably carried out under conditions of high stringency, and in particular at a temperature of 50° C. for 1 hour in a solution containing 8.823 gram/l of trisodium citrate-2H2O, 17.532 g/l of sodium chloride and 1% sodium dodecyl sulfate, or alternatively under the conditions described by Sambrook et al. (1989, pages 9.52–9.55).

A particular nucleic acid, for the purposes of the invention, encodes a polypeptide which comprises the sequence SEQ ID No.:9 or a fragment or derivative of this sequence, in particular the human FEBP1 protein. It is advantageously a nucleic acid which comprises the nucleic sequence SEQ ID No.:8.

The nucleic acids according to the invention can be used for producing the peptide compounds of the invention. The present application thus also relates to a method for preparing a peptide compound, according to which a cell which contains a nucleic acid according to the invention is cultured, under conditions for expression of said nucleic acid, and the peptide compound produced is recovered. In this case, the portion which encodes said polypeptide is generally placed under the control of signals which allow its expression in a host cell. The choice of these signals (promoters, terminators, secretion leader sequence, etc.) can vary as a function of the host cell used. Moreover, the nucleic acids of the invention can be part of a vector which can replicate autonomously, or which can integrate. More particularly, autonomously-replicating vectors can be prepared using sequences which replicate autonomously in the chosen host. As regards the integrating vectors, these can be prepared for example using sequences which are homologous to certain regions of the host genome, which allows the integration of the vector by homologous recombination. It can be a vector of plasmid, episomal, chromosomal, viral, etc. type.

The host cells which can be used for producing the peptides of the invention via the recombinant pathway, are both eukaryotic and prokaryotic hosts. Among the eukaryotic hosts which are suitable, mention may be made of animal cells, yeasts or fungi. In particular, as regards yeasts, mention may be made of yeasts of the genus Saccharomyces, Kluyveromyces, Pichia, Schwanniomyces or Hansenula. As regards animal cells, mention may be made of COS, CHO, C127, PC12 cells, etc. Among the fungi, mention may more particularly be made of Aspergillus ssp. or Trichoderma ssp. As prokaryotic hosts, use of the following bacteria is preferred: *E. coli*, Bacillus, or Streptomyces.

The nucleic acids according to the invention can also be used to prepare genetic antisense or antisense oligonucleotides which can be used as pharmaceutical or diagnostic agents. Antisense sequences are oligonucleotides of short length, which are complementary to the coding strand of a given gene, and which, for this reason, are capable of specifically hybridizing with the mRNA transcript, which inhibits its translation into a protein. A subject of the invention is thus the antisense sequences which are capable of at least partially inhibiting the interaction of the hnRNPL and/or FEBP1 proteins on the PTB1 domain of FE65. Such sequences can consist of all or part of the nucleotide sequences defined above. They are generally sequences or fragments of sequences which are complementary to sequences encoding peptides which interact with the PTB1 domain of FE65. Such oligonucleotides can be obtained by fragmentation or by chemical synthesis, etc.

The nucleic acid sequences can also be used in the context of therapies, for transferring and expressing, in vivo, antisense sequences or peptides which are capable of modulating the interaction of the hnRNPL and/or FEBP1 proteins with the PTB1 domain of FE65. In this respect, the sequences can be incorporated into viral or nonviral vectors, which allows their administration in vivo (Kahn, A. et al. 1991). As viral vectors in accordance with the invention, mention may be made most particularly of vectors of adenovirus, retrovirus, adenovirus-associated virus (AAV) or herpesvirus type. A subject of the present application is also defective recombinant viruses comprising a nucleic acid which encodes a (poly)peptide according to the invention.

The invention also allows the preparation of nucleotide probes which may or may not be synthetic, and which are capable of hybridizing with the nucleic acids defined above or with their complementary strand. Such probes can be used in vitro as a diagnostic tool, for detecting the expression or overexpression of the hnRNPL and/or FEBP1 proteins, or alternatively for detecting genetic abnormalities (incorrect splicing, polymorphisms, point mutations, etc.). These probes can also be used for detecting and isolating homologous nucleic acid sequences which encode peptides as defined above, using other cellular sources and preferably cells of human origin. The probes of the invention generally comprise at least 10 bases, and they can for example comprise up to the whole of one of the abovementioned sequences or of their complementary strand. Preferably, these probes are labeled prior to their use. For this, various techniques known to a person skilled in the art can be employed (radioactive, fluorescent, enzymatic, chemical labeling etc.).

A subject of the invention is also any pharmaceutical composition which comprises, as an active principle, at least one compound as defined above, in particular a peptide compound.

A subject of the invention is in particular any pharmaceutical composition which comprises, as an active principle, at least one antibody and/or one antibody fragment as defined above, as well as any pharmaceutical composition which comprises, as an active principle, at least one nucleic acid or one vector as defined above.

A subject of the invention is also any pharmaceutical composition which comprises, as an active principle, a chemical molecule which is capable of increasing or of decreasing the interaction between the hnRNPL and/or FEBP1 proteins and the FE65 protein.

Moreover, a subject of the invention is also pharmaceutical compositions in which the peptides, antibodies, chemical molecules and nucleotide sequences defined above are combined, mutually or with other active principles.

The pharmaceutical compositions according to the invention can be used to modulate the activity of the hnRNPL and/or FEBP1 proteins, and consequently, can modify the function of the APP, its intracellular transport, its maturation and its conversion into the β-amyloid peptide. More particularly, these pharmaceutical compositions are intended for modulating the interaction between the hnRNPL or FEBP1 proteins and the FE65 protein. They are more preferably pharmaceutical compositions which are intended for treating neurodegenerative diseases, such as for example Alzheimer's disease. The compositions (or compounds) of the invention are more particularly intended for inhibiting, at least partially, the interaction between the FE65 protein and the hnRNPL and/or FEBP1 protein.

A subject of the invention is also the use of the molecules described above for modulating the activity of the FE65 protein or for typing neurodegenerative diseases. In particular, the invention relates to the use of these molecules for modulating, at least partially, the activity of the PTB1 domain of FE65.

The invention also relates to a method for screening or characterizing molecules which have an action on the function of the FE65 protein, which comprises selecting molecules which are capable of binding the sequence SEQ ID No.:7 or the sequence SEQ ID No.:9, or a fragment (or derivative) of these sequences. The method advantageously comprises bringing the molecule(s) to be tested into contact, in vitro, with a polypeptide which comprises the sequence SEQ ID No.:7 or the sequence SEQ ID No.:9, or a fragment (or derivative) of these sequences, and selecting molecules which are capable of binding the sequence SEQ ID No.:7 (in particular the region between residues 1 and 349) or the sequence SEQ ID No.:9 (in particular the region between residues 1 and 337). The molecules tested can be of varied nature (peptide, nucleic acid, lipid, sugar, etc., or mixtures of such molecules, for example combinatory libraries, etc.). As indicated above, the molecules thus identified can be used to modulate the activity of the FE65 protein, and represent potential therapeutic agents for treating neurodegenerative pathologies.

Other advantages of the present invention will appear on reading the following examples. They should be considered as illustrations and nonlimiting.

MATERIAL AND TECHNIQUES USED

1) Yeast Strains Used:

The strain L40 of the genus *S. cerevisiae* (Mata. His3D200, trp1-901, leu2-3,112, ade2, LYS2:: (lexAop)4-

HIS3, URA3::(lexAop)8-LacZ, GAL4, GAL80) was used as a tool for screening the brain fusion library by the two-hybrid system. This strain enables the detection of a protein—protein interaction when one of the protein partners is fused to the LexA protein (Vojtek et al., 1993). It was cultured on the following culture medium:

Minimum YNB medium: Yeast Nitrogen Base (without amino acids) (6.7 g/l) (Difco)
Glucose (20 g/l) (Merck)

This medium can be solidified by addition of 20 g/l of agar (Difco).

To enable auxotrophic yeast to grow on this medium, it is necessary to add thereto the nitrogen-containing amino acids or bases on which they are dependent, at 50 mg/ml. 100 µg/ml of ampicillin are added to the medium to avoid bacterial contamination.

2) Bacterial Strains Used:

Strain TG1 of *Escherichia coli*, of genotype supE, hsdΔ5, thi, Δ(lacproAB), F'[traD36 pro A$^+$B$^+$lacI$^q$lacZΔM15] was used for constructing plasmids and for amplifying and isolating plasmids. It was cultured on the following medium:

LB medium:
  NaCl (5 g/l) (Sigma)
  Bactotryptone (10 g/l) (Difco)
  Yeast extract (5 g/l) (Difco)

This medium can be solidified by addition of 20 g/l of agar (Difco).

Ampicillin at 100 µg/ml was used to select the bacteria which had received the plasmids bearing the gene for resistance to this antibiotic, as marker.

3) Plasmids Used:

The vector pGAD10, supplied by Clontech® allows the expression, in the yeast, of fusion proteins in which fusion is between the transactivating domain of GAL4 and a protein which is encoded by the cDNA originating from a brain library.

The vector pLex9 (pBTM116) (Bartel et al., 1993) allows the expression, in the yeast, of fusion proteins in which fusion is with the protein LexA.

The vector pGAD424 (Clontech®) allows the expression, in the yeast, of fusion proteins in which fusion is with the transactivating domain of GAL4.

pLex-FE65PTB1; plasmid pLex9 which contains the sequence encoding the PTB1 domain of the FE65 protein (amino acids 395 to 543). This plasmid was used for screening protein partners of the PTB1 domain of FE65.

pLex-FE65PTB2; plasmid pLex9 which contains the sequence encoding the PTB2 domain of the FE65 protein (amino acids 565 to 698) which is known to interact with the cytoplasmic region of the APP (β-amyloid peptide precursor). This plasmid was used to test the specificity of interaction of the hnRNPL and FEBP1 proteins with the PTB domains of FE65.

pLex-HaRasVal12; plasmid pLex9 which contains the sequence encoding the HaRas protein which is mutated at position Val12, and which is known to interact with the mammalian Raf protein (Vojtek et al., 1993). This plasmid was used to test the specificity of interaction of the hnRNPL and FEBP1 proteins with FE65.

pGAD-Raf; plasmid pGAD424 which contains the sequence encoding the Raf protein (Vojtek et al., 1993). This plasmid was used to test the specificity of interaction of the hnRNPL and FEBP1 proteins with FE65.

pGAD-App; plasmid pGAD10 which contains the sequence encoding the cytoplasmic domain of the APP protein which is known to interact with the PTB2 domain of FE65 (Mercken et al., 1998). This plasmid was used to test the specificity of interaction of the hnRNPL and FEBP1 proteins with FE65.

4) Synthetic Oligonucleotides Used:

The oligonucleotides are synthesized using an Applied System ABI 394-08 machine. They are removed from the synthesis matrix with ammonia and precipitated twice with 10 volumes of n-butanol, then taken up in water. The quantification is carried out by measuring the optical density, SEQ ID No. 3: CTTCCCGGGTCCCCCACGGAATAC-CAAC SEQ ID No. 4: GGGGTCGACGGCATTACGCCGT-TCGGC These oligonucleotides made it possible to obtain the PCR fragment corresponding to the PTB1 domain of FE65 (represented on the sequence SEQ ID No. 1), and to introduce the sites XmaI and SalI at the ends (underlined).

SEQ ID No. 5: CCACTACAATGGATGATG

This oligonucleotide (GAL4TA) was used to sequence the inserts contained in the plasmids from the brain cDNA double-hybrid library.

5) Preparation of the Plasmid DNAs

The preparations of plasmid DNA, in small amounts and in large amounts, were carried out according to the protocols recommended by Quiagen, the manufacturer of the DNA purification kits:

Quiaprep Spin Miniprep kit, ref: 27106
Quiaprep Plasmid Maxiprep kit, ref: 12163.

6) Enzymatic Amplification of DNA by PCR (Polymerase Chain Reaction)

The PCR reactions are carried out in a final volume of 50 µl in the presence of the DNA matrix, of dNTP (0.2 mM), of PCR buffer (10 mM Tris-HCl pH 8.5, 1 mM MgCl$_2$, 5 mM KCl, 0.01% gelatin), of 0.5 µg of each one of the oligonucleotides and of 2.5 IU of Ampli Taq DNA polymerase (Perkin Elmer) with or without formamide (5%). The mixture is covered with 2 drops of liquid petroleum jelly, to limit the evaporation of the sample. The machine used is the "Crocodile II" from Appligene.

We used a matrix denaturation temperature of 90° C., a hybridization temperature of 50° C. and a temperature of elongation by the enzyme of 72° C.

7) Ligations

All the ligation reactions are carried out at +14° C. overnight in a final volume of 10 µl, in the presence of 100 to 200 ng of vector, 0.5 to 2 µg of insert, 40 IU of T4 DNA ligase enzyme (Biolabs) and a ligation buffer (50 mM Tris-HCl pH 7.8; 10 mM MgCl$_2$; 10 mM DTT; 1 mM ATP).

8) Transformation of Bacteria:

The transformation of bacteria with a plasmid is carried out according to the following protocol: the entire ligation volume (10 µl) is used to transform TG1 bacteria which are made competent by the method of Chung et al., (1988).

9) Separation and Extraction of the DNAs:

The separation and the extraction of the DNA fragments are carried out according to Sambrook et al., (1989).

10) Fluorescent Sequencing of the Plasmid DNAs

The sequencing technique used is derived from the method of Sanger et al., (1997), and is adapted for sequencing by fluorescence and developed by Applied Biosystems. The protocol used is that described by the designers of the system (Perkin Elmer).

11) Preparation of Plasmids from the Brain Library

This preparation was carried out according to the recommendations of the supplier (Clontech®).

12) Transformation of Yeast with a Plasmid

The yeast are made competent by treating with LiAC/PEG according to the method described by Gietz et al., (1995).

In the specific case of the transformation of yeast with the brain cDNA library, 250 ml, at $10^7$ cells/ml of a culture, in YNB+His+Lys+Ade+Leu minimum medium, of yeast containing the plasmid pLex-FE65 PTB1 is used. The yeasts, which are made competent according to the abovementioned protocol, are transformed with 30 μg of cDNA from the brain library. After the transformation steps, the yeasts are put back into culture in 250 ml of YNB+His+Lys+Ade+Leu at 28° C. for 16 hours, then recovered by centrifugation to be plated on a YNB+Lys+Ade medium and incubated for 3 days at 28° C. Determination of the efficacy of transformation and of the level of amplification was carried out according to the Clontech® protocol.

13) Extraction of the DNA (Genomic and Plasmid) from Yeast 3 ml of a yeast culture which has been incubated for 16 h at 30° C. are centrifuged and taken up in 200 μl of a lysis buffer (1M Sorbitol, 0.1M $KH_2PO_4/K_2HPO_4$ pH 7.4, 12.5 mg/ml zymolyase) and incubated for 1 h at 37° C. The lysate is then treated according to the protocol recommended by Quiagen, the manufacturer of the DNA purification kit; Quiaprep Spin Miniprep kit, ref: 27106.

14) β-galactosidase Activity Assay

A sheet of nitrocellulose is preplaced on the Petri dish containing the yeast clones, which are separated from each other. The sheet is then immersed in liquid nitrogen for 30 seconds to rupture the yeasts and thus to release the β-galactosidase activity. After thawing, the sheet of nitrocellulose is placed, colonies facing upwards, in another Petri dish containing a Whatman paper which has been presoaked in 1.5 ml of PBS solution (60 mM $Na_2HPO_4$, 40 mM $NaH_2PO_4$, 10 mM KCl, 1 mM $MgSO_4$, pH7) containing 15 μl of X-Gal (5-bromo-4-chloro-3-indoyl-β-D-galactoside) at 40 mg/ml of N,N-dimethylformamide. The dish is then placed in an incubator at 37° C. The test is taken to be positive when the colonies on the membrane turn blue after 6 hours.

EXAMPLE 1

Construction of an Expression Vector for a Fusion Protein in which Fusion is Between the PTB1 Domain of FE65 and the Lexa Protein Screening a library using the double-hybrid system requires the PTB1 domain of FE65 (FE65PTB1) to be fused to the LexA protein. The expression of this fusion protein is carried out using the vector pLex9, into which the sequence encoding the PTB1 domain of FE65 (SEQ ID No. 1 to 2) has been introduced, in the same reading frame as the sequence corresponding to the LexA protein.

The 448 bp-fragment of DNA which corresponds to amino acids 395 to 543 of the human FE65 protein (SEQ ID No.:2) was obtained by PCR using the oligonucleotides SEQ ID No. 3 and SEQ ID No. 4, which also allowed us to introduce the sites XmaI and SalI at the ends of the sequence. The PCR fragment was introduced between the XmaI and SalI sites of the multiple cloning site of the plasmid plex9, downstream of the sequence which corresponds to LexA, so as to give the vector pLex FE65PTB1.

The construct was verified by sequencing the DNA. This verification allowed us to show that this fragment has no mutations which were generated during the PCR reaction, and that it is fused in the same open reading frame as that of the fragment which corresponds to LexA.

EXAMPLE 2

Screening a Brain cDNA Fusion Library by the Two-hybrid Technique

We used the double-hybrid method (Fields and Song, 1989). Screening a fusion library makes it possible to identify clones which produce proteins which are fused with the transactivating domain of GAL4, and which are able to interact with the PTB1 domain of FE65. This interaction makes it possible to reconstitute a transactivator which will be capable of inducing the expression of the reporter genes His3 and LacZ in strain L40. To carry out this screening, we chose a fusion library which was prepared from human brain cDNA (Clontech®).

During the screening, it is necessary to maintain the probability that each separate plasmid of the fusion library is present in at least one yeast at the same time as the plasmid pLex-FE65PTB1. To maintain this probability, it is important to have a good efficiency of transformation of the yeast. For this, we chose a protocol for transforming yeast which gives an efficiency of $10^5$ cells transformed per μg of DNA. In addition, as the cotransformation of the yeast with two different plasmids reduces this efficiency, we preferred to use a yeast which was pretransformed with the plasmid pLex-FE65PTB1. This strain L40-FE65PTB1, of phenotype His-, Lys-, Ade-, Leu-, was transformed with 30 μg of plasmid DNA from the fusion library. This amount of DNA allowed us to obtain, after estimation, $2.8 \times 10^6$ transformed cells, which corresponds to a number which is slightly higher than the number of separate plasmids that constitutes the library. According to this result, we can consider that virtually all of the plasmids of the library were used to transform the yeasts. The selection of the transformed cells which are capable of reconstituting a functional GAL4 transactivator was done on a YNB+Lys+Ade medium.

At the end of this selection, 97 clones having a His+ phenotype were obtained. A β-galactosidase activity assay was carried out on these transformants to determine the number of clones which express the other reporter gene, LacZ. Out of 97 clones obtained, 27 had the double phenotype His+, βGal+, which thus shows that they express proteins which are able to interact with the PTB1 domain of FE65.

EXAMPLE 3

Isolation of the Brain Library Plasmids from the Yeast Clones Selected

To identify the proteins which are able to interact with the PTB1 domain of FE65, we extracted the fusion library plasmids contained in the yeast which were selected during the double-hybrid screening. In order to be able to obtain a large amount thereof, this isolation requires a prior transformation of E. coli with an extract of DNA from the positive yeast strains. As the library plasmid which is contained in this extract is a yeast/E.coli shuttle plasmid, it can easily replicate in the bacterium.

The plasmid DNAs from the bacterial colonies obtained after transformation with yeast DNA extracts, were analyzed by digestion with restriction enzymes and separation of the DNA fragments on an agarose gel. Out of the 23 clones analyzed, we obtained 6 different restriction profiles, of which two were highly represented. These results showed that at least 6 different plasmids were isolated during the screening; we focused more particularly on the DNA fragment originating from the cDNA library which is contained in the two most represented (8 and 4 times) plasmids.

EXAMPLE 4

Determination of the Sequence of the Inserts of the Plasmids Identified

Sequencing was carried out on the 2 most represented plasmids using the oligonucleotide GAL4TA (SEQ ID No.

5), which is complementary to the GAL4TA region, close to the insertion site of the brain cDNA library, at 52 bp from the EcoRI site.

Comparison of the sequence of the first plasmid selected with the sequences contained in the databanks GENBank and EMBL (European Molecular Biology Lab) showed that the sequence of the cDNA which is present in this first plasmid shows more than 99% identity, at the nucleotide level, with the human gene which encodes the hnRNPL protein, having the access number: NP_001524/g4557645. The sequence of this gene, which we cloned by the two-hybrid system, begins at nucleotide 346, which corresponds to the $116^{th}$ amino acid, and ends at nucleotide 1392, which corresponds to the $464^{th}$ amino acid which is located 58 amino acids from the end of the hnRNPL protein (SEQ ID No.:6 and 7). This result shows that the domain of interaction of hnRNPL with the human FE65 protein is contained in the central region of hnRNPL. This region contains a sequence of type NPXY, which is known to be the consensus site of binding of the PTB domains (Borg et al., 1996). The hnRNPL sequence (SEQ ID No. 6 to 7) which we cloned differs from the published sequence (Pinol-Roma et al., 1989) by the substitution of a guanine with thymidine at position 748, which leads to the changing of a glycine into cysteine at the $250^{th}$ amino acid of the sequence SEQ ID No. :6, which corresponds to nucleotide 1093 and to amino acid 365 of the whole hnRNPL protein.

Comparison of the sequence of the second plasmid selected with the sequences contained in the databanks GENBank and EMBL (European Molecular Biology Lab) showed that the sequence of the cDNA which is contained in this plasmid shows no significant homology with the sequences contained in these databanks. This sequence (SEQ ID No. 8 to 9) of 1275 nucleotides has a stop codon at position 1012, and encodes a peptide of 337 amino acids. The protein which corresponds to this sequence was named FEBP1 for FE65 Binding PTB1 domain protein.

EXAMPLE 5

Analysis of the Specificity of Interaction Between the PTB Domains of FE65 and the hnRNPL And FEBP1 Proteins To determine the specificity of the interaction between the PTB1 and PTB2 domains of the human FE65 protein and the hnRNPL and FEBP1 proteins, we carried out an interaction assay by the two-hybrid method, using the plasmid pLex-FE65PTB2 which encodes the PTB2 domain of FE65 fused to the LexA protein, in place of the plasmid pLex-FE65PTB1. An absence of interaction between the PTB2 domain and these two proteins would make it possible to show a specificity of interaction with the PTB1 domain of FE65.

To carry out this assay, we transformed strain L40 with the plasmids which were isolated during the screening of the brain cDNA library, and with the plasmid pLex-FE65PTB2. Controls for specificity of interaction were also carried out, by transforming this strain with different plasmids as indicated in table No. 1. A βGal activity assay was carried out on the cells which were transformed with the various plasmids, in order to detect a protein—protein interaction. All the plasmid combinations, and thus the interactions, which were tested in the double-hybrid system are reported in Table No. 1. The plasmid combinations and the corresponding type of vector (pLex or pGAD) are indicated in the columns "Plasmid Combinations". The + sign and − sign in the "Interaction" column correspond to the results of the βGal assay, and indicate respectively the detection or the nondetection of protein—protein interaction.

According to the result of the assay (cf. Table No. 1), only the two yeasts which were transformed with the two plasmids isolated from the brain cDNA library and with the plasmid pLex-FE65PTB1 had βGal+ activity, which thus shows that among the two PTB domains of FE65, only the PTB1 domain interacts with the central portion of hnRNPL or the fragment of the FEBP1 protein. The PTB1 domain of FE65 appears to interact specifically with hnRNPL and FEBP1, since we were unable to show interactions with the HaRasVal12 protein or the C-terminal domain of the APP, by the two-hybrids technique.

BIBLIOGRAPHIC REFERENCES

Bartlet, P. L., C. -T. Chien, R. Strenglanz and S. Fields, 1993 D. A. Hartley Ed, Oxford University press: 153.

Borg, J. -P. Ooi, E. Levy and B. Margolis, 1996. The Phosphotyrosine Interaction Domains of X11 and FE65 Bind to Distinct Sites on the YENPTY Motif of Amyloid Precursor Protein. Mol. Cell. Biol. 16: 6229–6241.

Borg, J. -P., Y. Yang, M. De Taddeo-Borg, B. Margolis and R. S. Turner, 1998. The X11a protein Slows Cellular Amyloid Precursor Protein Processing and Reduces Aβ40 and Aβ42 Secretion. J. Biol. Chem. 273: 14761–14766.

Bressler, S. L., M. D. Gray, B. L. Sopher, Q. Hu, M. G. Hearn, D. G. Pham, M. B. Dinulos, K.-I. Fukuchi, S. S. Sisodia, M. A. Miller, C. M. Disteche and G. M. Martin, 1996. cDNA cloning and chromosome mapping of the human Fe65 gene: interaction of the conserved cytoplasmic domains of the human β-amyloid precursor protein and its homologs with the mouse Fe65 protein. Hum. Mol. Genet. 5: 1589–1598.

Chung, C. T., E. L. Suzann, and R. H. Miller, 1989. One-step preparation of competent Escherichia coli: transformation and storage of bacterial cells in the same solution. Proc. Natl. Acad. Sci. USA, 86: 2172–2175.

Duilio, A., R. Faraonio, G. Minopoli, N. Zambrano and T. Russo. 1998. Fe65L2 a new member of the Fe65 protein family interacting with the intracellular domain of the Alzheimer's β-amyloid precursor protein. Biochem. J. 330: 513–519.

Ermekova, K. S., N. Zambrano, H. Linn, G. Minopoli, F. Gertler, T. Russo and M. Sudol. 1997. The WW Domain of Neural Protein FE65 Interacts with Proline-rich Motifs in Mena, the Mammalian Homolog of Drosophila Enabled. J. Biol. Chem. 272: 32869–32877.

Fields, S. and O. Song. 1989. A novel genetic system to detect protein—protein interactions. Nature. 340: 245–246.

Fiore, F., N. Zambrano, G. Minopoli, V. Donini, A. Duilio and T. Russo. 1995. The Regions of the Fe65 Protein Homologous to the Phosphotyrosine Interaction/Phosphotyrosine Binding Domain of Shc Bin the Intracellular Domain of the Alzheimer's Amyloid Precursor Protein. J. Biol. Chem . 270: 30853–30856.

Gietz, R. D., R. H. Schiestl, A. R. Willems, and R. A Woods. 1995 Studies on the transformation of intact yeast cells by LiAC/SS-DNA/PEG procedure. Yeast, 11: 355–360.

Golde, T. E., S. Estus, L. H. Younkin, D. J. Selkoe and S. G. Younkin, 1992. Processing of the amyloid protein precursor to potentially amyloidogenic derivatives. Science 255: 728–730.

Guenette, S. Y., J. Chen, P. D. Jondro and R. E. Tanzi. 1996. Association of a novel human FE65-like protein with the cytoplasmic domain of the b-amyloid precursor protein. *Proc. Natl. Acad. Sci. U.S.A.* 93: 10832–10837.

Guenette, S. Y., J. Chen, A. Ferland, C. Haass, A. Capell and R. E. Tanzi. 1999. HFE65L. Influences Amyloid Precursor Protein Maturation and Secretion. *J. Neurochem.* 73: 985–993.

Koo, E. H., and S. L. Squazzo, 1994. Evidence that production and release of amyloid beta-protein involves the endocytic pathway. *J. Biol. Chem.* 269: 17386–17389.

Kahn, A. 1991 Therapie genique: espoirs et limites. *Medecine et Sciences.* 7: 705–714.

McLoughlin, D. M. and C. C. J. Miller. 1996. The intracellular cytoplasmic domain of the Alzheimer's disease amyloid precursor proteins in the yeast two-hybrid system. *FEBS Lett.* 397: 197–200.

Mercken, L., M. Bock, J. Menager, X. Franco, M.-F. Paul, L. Pradier and A. Fournier. 1998. FE65 and COFE65: two proteins interacting with the cytoplasmic domain of APP. *Neurobiol. Aging* 19: S37.

Perez, R. G., S. Soriano, J. D. Hayes, B. Ostaszewski, W. Xia, D. J.Selkoe, X. Chen, G. B. Stokin, and E. H. Koo. 1999. Mutagenesis identifies new signals for beta-amyloid precursor protein endocytosis, turnover, and the generation of secreted fragments, including Abeta42. *J. Biol. Chem.* 274: 18851–18856.

Pinol-Roma, S., M. S Swanson, J. G. Gall, and G. Dreyfuss. 1989. A novel heterogeneous nuclear RNP protein with a unique distribution on nascent transcripts. *J. Cell Biol.* 109: 2575–2587.

Sabo, S. L., L. M. Lanier, A. F. Ikin, O. Khorkova, S. Sahasrabudhe, P. Greengard and J. D. Buxbaum. 1999. Regulation of the β-Amyloid Secretion by FE65, an Amyloid Protein Precursor-binding Protein. *J. Biol. Chem.* 274: 7952–7957.

Sambrook, J., E. F. Fritsch, and T. Maniatis. 1989. Molecular Cloning, A laboratory manual. Second Edition, Tome I, II, III. Cold Spring Harbor Laboratory Press.

Sanger, F., S. Nicklen, and A. R. Coulson, 1997. DNA sequencing with Chain Terminating Inhibitors. *Proc. Natl. Acad. Sci. USA,* 74: 5463–5467.

Sastre, M., R. S. Turner, and E. Levy. 1998. X11 Interaction with β-Amyloid Precursor Protein Modulates Its Cellular Stabilization and Reduces Amyloid β-Protein Secretion. *J. Biol. Chem.* 273: 22351–22357.

Tanahashi, H. And T. Tabira. 1999a X11L2, a new member of the XII protein family, interacts with Alzheimer's beta-amyloid precursor protein. *Biochem. Biophys. Res. Commun.* 255: 663–667.

Tanahashi, H., and T. Tabira. 1999b. Genome Structure and Chromosomal Mapping of the Gene for FE65L2 Interacting with Alzheimer's β-Amyloid Precursor Protein. *Biochem. Biophys. Res. Commun.* 258: 385–389.

Tanahashi, H., and T. Tabira. 1999c. Molecular cloning of human Fe65L2 and its interaction with the Alzheimer's beta-amyloid precursor protein. *Neurosc. Lett.* 261: 143–146.

Trommsdorff, M., J. -P. Borg, B. Margolis and J. Herz. 1998. Interaction of Cytosolic Adaptor Proteins with Neuronal Apolipoprotein E. Receptors and the Amyloid Precursor Protein. *J. Biol. Chem.* 273: 33556–33560.

Vojtek, A. B., S. M. Hollenberg, and J. A. Cooper. 1993. Mammalian Ras interacts directly with the serine/threonine kinase Raf. *Cell* 74: 205–214.

Zambrano, N., J.D. Buxbaum, G. Minopoli, F. Fiore, P. De Candia, S. De Renzis, R. Faraonio, S. Sabo, J. Cheetham, M. Sudol and T. Russo. 1997. Interaction of the Phosphotyrosine Interaction/Phosphotyrosine Binding-related Domains of Fe65 with Wild-type and Mutant Alzheimer's β-Amyloid Precursor Proteins. *J. Biol. Chem.* 272: 6399–6405.

Yankner, B. A. 1996. Mechanisms of neuronal degeneration in Alzheimer's disease. Neuron 16: 921–932.

TABLE No. 1

| PLASMID COMBINATION | | |
|---|---|---|
| pLex | pGAD | INTERACTION |
| FE65PTB1 | hnRNPL | + |
| FE65PTB1 | FEBP1 | + |
| FE65PTB1 | APP | − |
| FE65PTB1 | Raf | − |
| FE65PTB2 | hnRNPL | − |
| FE65PTB2 | FEBP1 | − |
| FE65PTB2 | APP | + |
| FE65PTB2 | Raf | − |
| HaRasVal12 | hnRNPL | − |
| HaRasVal12 | FEBP1 | − |
| HaRasVal12 | APP | − |
| HaRasVal12 | Raf | + |

---

What is claimed is:

1. An isolated nucleic acid that encodes a polypeptide comprising the amino acid of SEQ ID NO:9.

2. The isolated nucleic acid of claim 1, comprising the nucleotide sequence of SEQ ID NO: 8.

3. A vector comprising the isolated nucleic acid of claim 1.

4. A vector comprising the isolated nucleic acid of claim 2.

5. The vector of claim 3, wherein said vector is an expression vector and said isolated nucleic acid is operatively associated with an expression control signal.

6. A host cell transformed or transfected with the expression vector of claim 5.

7. A method for producing a polypeptide comprising the amino acid sequence of SEQ ID NO:9, comprising the steps of (a) culturing the host cell of claim 6 under conditions for expression of the isolated nucleic acid; and (b) recovering the polypeptide.

8. The vector of claim 4, wherein said vector is an expression vector and said isolated nucleic acid is operatively associated with an expression control signal.

9. A host cell transformed or transfected with the expression vector of claim 8.

10. A method for producing a polypeptide comprising the amino acid sequence of SEQ ID NO: 9, comprising the steps of:

(a) culturing the host cell of claim 9 under conditions for expression of the isolated nucleic acid; and (b) recovering the polypeptide.

11. An isolated polypeptide comprising the amino acid sequence of SEQ ID NO: 9.

* * * * *